United States Patent [19]

Milly

[11] 4,135,092

[45] Jan. 16, 1979

[54] METHOD OF QUANTIFYING FUGITIVE EMISSION RATES FROM POLLUTION SOURCES

[75] Inventor: George H. Milly, Potomac, Md.

[73] Assignee: Geomet Exploration, Inc., Boulder, Colo.

[21] Appl. No.: 895,427

[22] Filed: Apr. 12, 1978

[51] Int. Cl.² .................... G01J 1/00; G01N 31/00
[52] U.S. Cl. ............................. 250/343; 250/345; 73/23
[58] Field of Search ............... 250/341, 343, 344, 345; 356/51, 96, 201, 186; 73/23, 28, 170 R, 432 R

[56] References Cited

U.S. PATENT DOCUMENTS

| B 532,679 | 4/1976 | Pretet | 73/170 A |
|---|---|---|---|
| 2,390,739 | 12/1945 | Scherbatskoy | 73/170 R |
| 2,468,021 | 4/1949 | Black | 73/28 |
| 2,645,941 | 7/1953 | Reid | 73/170 R |
| 3,229,517 | 1/1966 | Smith | 73/170 R |
| 3,670,572 | 6/1972 | Devereux et al. | 73/170 R |
| 3,820,897 | 6/1974 | Roess | 356/75 |
| 4,056,969 | 11/1977 | Barringer | 73/28 |

Primary Examiner—Alfred E. Smith
Assistant Examiner—Janice A. Howell
Attorney, Agent, or Firm—David H. Semmes

[57] ABSTRACT

Method of quantifying fugitive emission rates, such as those emanating from factories, office buildings, and the like. The method is characterized by its ability to quantify airborne fugitive emissions by defining a vertical profile of pollutant flux downwind of pollution sources. The method is thus a major improvement over conventional quasi-stack, roof monitor and upwind-downwind techniques of measuring pollutions. The method is characterized by its ability to quantify fugitive emission rates, regardless of source emission characteristics or topography.

16 Claims, 9 Drawing Figures

VARIATION OF POLLUTANT CONCENTRATION
CROSSWIND AT A HEIGHT Z, AND AT A DISTANCE
X DOWNWIND OF THE POLLUTANT SOURCE

FUGITIVE EMISSION RATE, UNADJUSTED
FOR SAMPLING RATE AND TRAVERSE SPEED

LONG PATH INFRA-RED ABSORPTION TECHNIQUE
OF MEASURING CROSSWIND INTEGRATED
CONCENTRATION

METHOD OF QUANTIFYING FUGITIVE EMISSION RATES FROM POLLUTION SOURCES

BACKGROUND OF THE INVENTION

Field of the Invention

Pollution control, particularly methods for quantification of airborne fugitive emissions. Traditionally, such fugitive emissions are measured by one or more of the following techniques:

1. The quasi-stack method involves the installation of a hood over an isolatable source so that the pollutant is transmitted through a duct of known cross-section thereby permitting application of standard stack sampling (confined source) techniques involving measurement of flow rate and pollutant concentration. This approach therefore involves conversion of an element of fugitive emission into a confined emission but is seriously limited since it is not a practical approach for the case of a multiplicity of emission points or for large sources; or for disseminated area sources; or for complex, variable and ill-defined operations, as described above.

2. The roof monitor method is applicable to pollutants generated within a building which enter the atomsphere through an opening in the building. This is a version of stack sampling (confined emission) where the opening is so large that pollutant concentrations and flow rates must be measured at a number of points over the plane of the opening and then integrated to obtain the total emission rate into the atmosphere. This approach is applicable only to the case of pollutants generated indoors, and where there is a large but well-defined opening to the atmosphere. It is not useful for a multiplicity of emission points, for disseminated sources, or for complex, variable and ill-defined operations as described above.

3. The upwind-downwind method is based on measuring atmospheric concentrations downwind of the emission source, as well as upwind, and attributing the difference to the source. The critical element in this technique is the use of mathematical models of atomspheric diffusion along with meteorological measurements to back-calculate source strength. Of the three general methods, this is the only one which in principle has any capability for dealing with the case of unconfined sources. The limitations on the method, however, are significant. First, it must be presumed that the atmospheric diffusion model is accurate in describing behavior of pollutants after release into the atmosphere. Generally speaking, even for the simplest case of a ground level, continuous point source, the agreement between model and observation is only approximate. Second, the method is incapable of treating the more common problems represented by emission sources of arbitrary and irregular geometry, including multiple elements at various heights. This is so because diffusion formulae characteristically are available only for simple source geometries such as point, line, uniform area, or normally distributed sources. The practical problem to be confronted, however, is that of complex, multiple, non-uniform and unconfined pollution sources. Particularly, the absence of prior knowledge of the spatial distribution of pollution source strength elements, which might otherwise permit mathematical integration of the simple diffusion formulae, -- prohibits quantification of fugitive emissions. Spatial distribution of source strength, of course, is one of the very objectives which fugitive source evaluation seeks to measure.

In summary, none of the available methods is capable of providing a direct measurement of pollution emission rates for the case of unconfined, fugitive sources of arbitrary and complex geometry.

DESCRIPTION OF THE PRIOR ART

Being submitted under the provisions of 37 C.F.R. 1.97.

SUMMARY OF THE INVENTION

According to the present method, airborne fugitive emissions are quantified by gauging wind velocity and direction at an index point downwind of a pollution source and outlining near the index point a pollution detection plane oriented transversely with respect to the wind. Pollutant concentration is sensed within the vertical and lateral confines of the pollution detection plane and quantified as a vertical profile of pollutant flux. This quantifying may be related to actual time of emission by consideration of distance from the pollution source and wind speed.

DESCRIPTION OF THE PREFERRED EMBODIMENTS

1. The Problem

Figure 1:
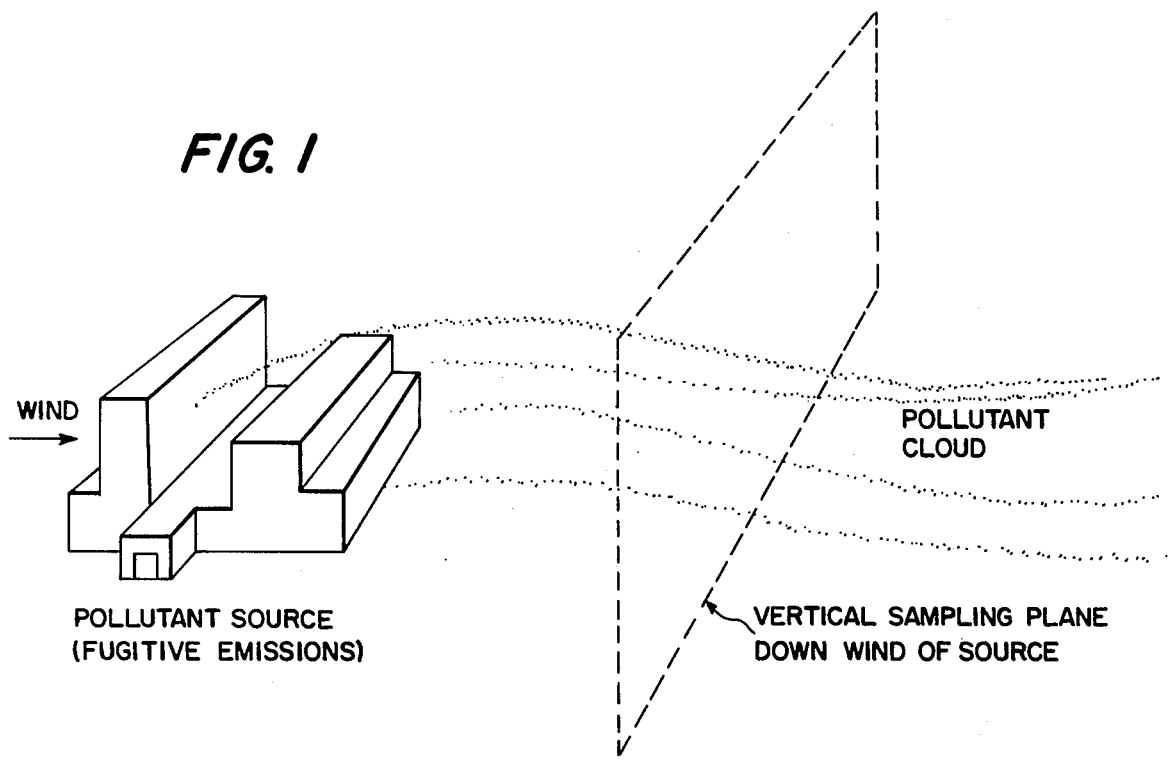
FIG. 1 is a schematic showing a pollution detection plane, defined downwind of a pollution source for vertical sampling, so as to quantify pollutant flux.

The evaluation and control of atmospheric pollution is ultimately based on the capability to measure various aspects of its occurrence. Without such a capability there can be no quantitative means for ascertaining degree of improvement, nor can diagnostic information be made available to provide guidance concerning effective approaches toward control. One of the most critical requirements is the ability to measure the rate of emission of pollutants of interest from the various types of sources giving rise to their presence.

Differentiation of types of pollution sources is of special importance, since each presents specific problems with regard to measurement and evaluation. Examples of commonly encountered sources are industrial or factory chimneys, power plant stacks, aircraft operations, refineries, foundries, steel furnaces, coking operations, industrial complexes, cement plants, automobiles, etc. When the problem of measuring source emission rates is considered, the diversity of source types may be reduced to a fewer number, according to the conceptual approach to evaluation which is appropriate in each case.

The principal distinction to be made is between emissions which take place through a confined space such as a chimney or exhaust pipe or other well defined duct, and those emissions which are disseminated over an area or arise from a multiplicity of ill-defined source elements or operations. From the measurement point of view the distinction is sharp. In the first case of "confined emissions" the rate of emission is obtained by measuring the volume flow rate of air through a confined exit port (chimney, exhaust pipe) and, concurrently, the concentration of the pollutant of interest in the exit port. The product of these two quantities times the cross-sectional area of the exit port is the rate of emission.

In the second case, commonly referred to as "fugitive emissions," there is no single exit port. Rather, there may be a multiplicity of emission points (such as leakage through various open or closed door and windows, cracks, joints, ventilators, etc. of an industrial building); or there may be a widespread, disseminated source region open to the atmosphere and consequently with no exit ducts or ports (such as tailing ponds with volatile components, industrial dump areas subject to wind-borne dust propagation, uranium stockpiles with radon emanation, forest stands emitting water vapor through evapotranspiration); or they may be complex, variable and ill-defined operations with variable proportions between indoors and outdoors (such as cement plants, grading and earth moving operations, complexes of individual sources, as might be represented by automobiles and aircraft in an airport area).

The measurement of emission rate for "fugitive sources" presents a quite different problem from the case of "confined sources" because it is not practicable, in general, to define the volume flow rate and concurrent concentration for each emission element. Indeed there may not exist any exit points at all, as in the case of outdoor operations. As a result, the presently available approaches to measuring fugitive emission rates are either partial or indirect, and are subject to a high degree of uncertainty. The principle conventional approaches as recently summarized by Statnick and Kolnsberg (Journal of the Air Pollution Control Association, November 1976, pp. 1047-1049) are: (a) the quasi-stack method, (b) the roof monitor method, and (c) the upwind-downwind method.

2. Proposed Solution

Instead of attempting to transform a fugitive source into a confined source (which is only applicable to a very limited range of such sources), applicant approaches the problem in a manner which is completely general, does not involve the complexity and logistic effort involved in such transformations, and which avoids the indirectness and uncertainties involved in the upwind-downwind method. This is accomplished by employment of a system of measurement designed to observe the flux of pollutant through a vertical plane defined at an arbitrary distance downwind of all active elements of the fugitive source, extending from ground level vertically upward sufficiently high to encompass all effluent arising from the source, and extending crosswind in both directions sufficiently to include all effluent arising from the source (See FIG. 1).

The concept of employing sampling points distributed over a vertical surface oriented crosswind has been successfully tested by the inventor in evaluating the dissemination efficiency of chemical and biological weapons, which result in emission sources of complex and varied geometry in the unconfined atmosphere, produced by a variety of exploding, thermal generating and atomizing mechanisms, either simply or in multiple arrays of a random nature (See G. H. Milly, International Journal of Air and Water Pollution, 1964, Vol. 8, pp. 291-295). In proving the concept, the sampling array in these military applications consisted of a series of sampling masts, with air samplers emplaced at intervals along the mast. Sampling at each point consisted either of a single total dosage integrating sampler or a succession of short-time samples depending on the time-varying nature of the source. Concurrent measurement of the vertical distribution of wind speed permits calculation of the pollutant flux rate through the sampling plane according to the following principles.

We consider a source located at the origin of a rectangular co-ordinate system oriented with the x-axis in the direction of the mean wind, the y-axis crosswind and the z-axis vertically. For the general case of an emission rate which varies with time, the cumulative flux of contaminant transported up to time $\tau$, through a plane located at x = constant, downwind of the source, $$Q(\tau) = \int_0^\infty \int_{-\infty}^\infty \int_0^\tau C(y,z,t)\, u(z,t)\, dt\, dy\, dz \tag{1}$$

where u(z,t) and C(y,z,t) are the wind speed and concentration of pollutant, respectively; and wind speed u is taken to be invariant in y provided the crosswind dimension of the source is not too great. Otherwise the wind profile may be obtained at more than one location. Since $Q(\tau)$ is measured at a distance x downwind, it corresponds to the cumulative release at the source at time $(\tau - x/u)$. If the vertical plane is not too far downwind of the source, and if $\tau$ is not too short (i.e., if $\tau >> x/u$), the total transport through the plane may be taken as a good approximation to the cumulative release at the source at time $\tau$. It may not always be readily feasible to determine experimentally the value of the inner integral in equation (1) because of the implied requirement for large numbers of continuous records of concentration. However, under the assumption of n sequential samples at each sampling point, sufficiently short that wind speed or concentration may be considered constant over the sampling interval, equation (1) may be approximated by $$Q(\tau) = \sum_{i=1}^n \int_0^\infty u_i(z) \int_{-\infty}^\infty D_i(y,z)\, dy\, dz \tag{2}$$

where $D_i$ is the dosage increment in the i'th time interval, measured over a grid of sample points in a yz-plane normal to the wind direction, by vacuum-aspiration and collection of the pollutant by appropriate means (such as sampling bubblers, impactors, filters, etc.), followed by analysis of bubbler, impactor or filter contents.

In practice, it was found convenient to employ a cylindrical surface rather than a plane in the case of fixed emplacement of a sampling grid so as to allow ready accommodation of any wind direction. This arrangement gives a slightly distorted estimate of the true crosswind dosage distribution, since measurements are made along an arc and not a crosswind line. However, typical corrections, based on considering the projected sample spacing on a chord, amount to less than 4 percent.

While the underlying scientific concept of evaluating fugitive sources has been demonstrated as described above, conventional mechanical arrangements have not been readily adaptable to the evaluation of a multiplicity of types of fugitive sources in a variety of locations. The mechanical system employed in proving the concept consisted of a permanent emplacement of such complexity as not to be suitable for a flexible approach to varying requirements of fugitive source assessment.

It is the purpose of this invention to provide a means of evaluating mass flux of a pollutant through a vertical plane oriented crosswind, and downwind of a fugitive source, by means which are practical, economical, flexible, and which do not require the emplacement around such sources of complex and permanent or semi-permanent measurement systems, and which avoid the deficiencies of presently available approaches.

The central methodological component of the invention involves measurement of the crosswind integrated concentration in such a way that neither permanent nor semi-permanent nor extensive emplacement of air sampling instrumentation is required.

The theoretical basis of the invention is obtained by recasting equation (1) as follows:

$$Q(t) = \int_0^\infty \int_{-\infty}^\infty C(y,z,t) \, u(z,t) \, dy \, dz \tag{3}$$

where $Q(t)$ = rate of pollution flux at any time t.
Concentration measurements are made over a sufficiently short time that wind speed u and concentration C may be assumed constant during the period of measurement. We may then write equation (3) as $$Q = \int_0^\infty u(z) \int_{-\infty}^\infty C(y,z) \, dy \, dz \tag{4}$$

We designate the inner integral of equation (4) as the crosswind integrated concentration, i.e., $$K(z) = \int_{-\infty}^\infty C(y,z) \, dy \tag{5}$$

so that $$Q = \int_0^\infty u(z) \, K(z) \, dz \tag{6}$$

The determination of $K(z)$ is done under this invention by any one of several mechanical procedures. Each employs a vertical array of sampling instruments (either sensors and associated continuous concentration recorders, or sampling ports associated with devices for collecting samples) at a series of heights above ground, mounted on a single vertical support, the support being translated crosswind at a convenient distance downwind of the fugitive source. In some cases where the emission rate is reasonably constant, traverses by a single sensor or collector may be made sequentially at a series of heights.

Figure 2:
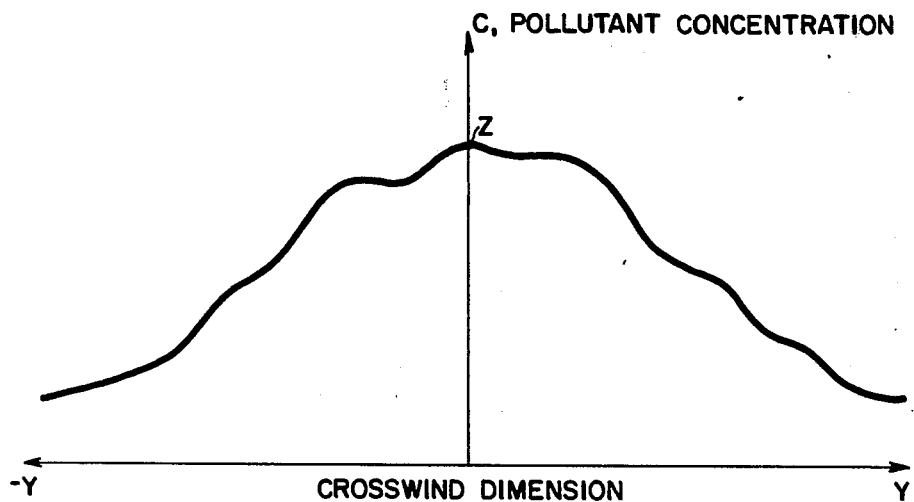
FIG. 2 is a graph displaying a horizontal profile of pollutant concentration along axis Y—Y, at a height Z and at a distance X downwind of the pollutant source.

If the sampling device is translated crosswind at a speed such that the distribution of concentration crosswind may be assumed to be constant during the traverse, then the total amount of pollutant collected may be related to the crosswind integrated concentration, as follows:

Consider that there exists a distribution of concentration crosswind such as in FIG. 2. We assume a constant sampling volume flow rate V, and a constant crosswind traversal speed v of the sampling port, while sampling the crosswind concentration distribution $C(y,z)$ at a height z above ground.

In traversing interval dy, the sampler collects an increment of material given by $$dq = VC(y) \, dt \tag{7}$$

but $$dt = dy/v \tag{8}$$

so that $$dq = (VC(y) \, dy/v) \tag{9}$$

and the amount of pollutant collected by the sampler during the traverse at height z is $$q(z) = \frac{V}{v} \int_{-\infty}^\infty C(y) \, dy \tag{10}$$

and by reference to equation (5)

$$q(z) = (V/v) K(z) \tag{11}$$

from which the crosswind integrated concentration can be obtained, knowing the amount of material collected, the sampling flow rate and the crosswind traversal rate of the sampling port:

$$K(z) = \frac{q(z) \, v}{V} \tag{12}$$

In the case of direct reading sensors, where material is not physically collected, $K(z)$ is obtained directly from the trace of concentration vs. distance by numerical integration of the record.

By making concurrent sampling traverses at a series of heights, and a simultaneous measurement of the wind speed profile with height, we may make use of equation (6) to obtain the desired fugitive emission rate:

$$Q = \frac{v}{V} \int_0^\infty u(z) \, q(z) \, dz \tag{13}$$

Figure 3:
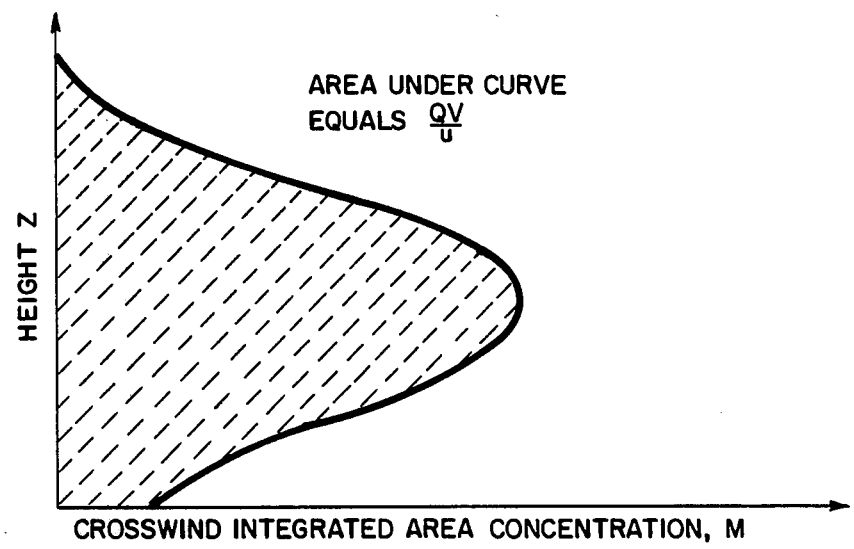
FIG. 3 is a graphical integration to obtain fugitive emission rate, unadjusted for sampling rate and traverse speed.

Equation (13) is evaluated numerically, making use of the observed values of u and q at a series of heights. An example is afforded by a graphical procedure. The product uq is calculated for each sampling height to obtain values of M, which we define as the crosswind integrated area concentration, and which are then plotted as in FIG. 3. The shape of the illustrative curve in FIG. 3 corresponds to a complex of source points where the major emissions occur at heights above ground level. The area under the curve of FIG. 3 may be measured, e.g., planimetrically, to obtain the integral in equation (13). This value, when multiplied by v/V gives the fugitive emission rate which is sought.

The mechanical means for obtaining the required values of q through use of sampling instrumentation can be any one of several, and the choice will be dependent on the circumstances of the particular situation being evaluated. In every case, however, there is required a sample collector or sensor at each sampling height, and a means of supporting the samplers to permit concurrent or rapidly successive traverse. The choice of sampler or sensor is dependent on the nature of the pollutant. Various vacuum-aspirated, liquid-filled bubbler devices may be employed for collecting gaseous pollutants. Particulate pollutants may be collected by use of impinger bubblers, impactors, or filters. All of these approaches are compatible with the method of this invention.

Mechanical systems for implementing the invention incorporate:

(a) a means for moving pollution sensing or collecting instrumentation crosswind at a series of heights above ground sufficient to encompass the vertical extent of the pollution cloud.

(b) a means for measuring the vertical profile of wind speed and direction over the height interval in which pollution sampling is conducted.

Figure 4:
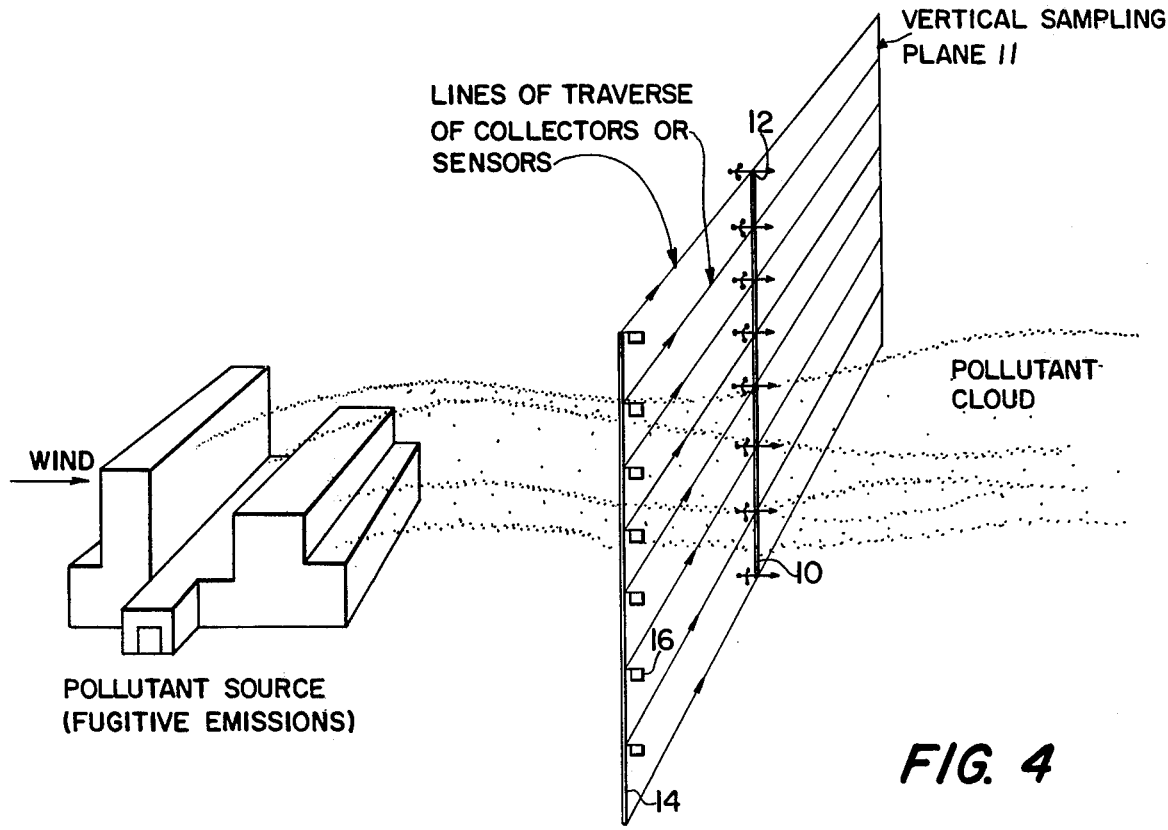
FIG. 4 is a schematic, showing wind gauging and pollution sensing components of a suggested fugitive emission rate measuring system.

These components are represented schematically in the system diagram of FIG. 4.

The measurement of wind profiles can be accomplished by conventional hardware, including portable, extensible masts for supporting wind direction and speed sensors and corresponding recording equipment, or by well known pilot balloon observational systems, including both single theodolite and double theodolite tracking methods, when height intervals beyond the practical limits of readily collapsed and portable instrument support masts are encountered. Such instrumentation and hardware is compatible with the adaptable and flexible nature of the measurement system for fugitive emissions which is the subject of this invention.

In FIG. 4 a pollution detection or vertical sampling plane 11 is illustrated as defined at an arbitrary index point, downwind of a fugitive source region, such as a factory or the like. A plurality of sample collectors or sensors 16 may be mounted upon a vertical support 14 so as to define lines of sensing traverse within the vertical and lateral confines of the pollution detection plane.

The pollution detection plane may be oriented crosswind of the pollutant cloud by means of a plurality of wind speed and direction sensors or anemometers 12, mounted upon wind profile mast 10. Mast 10 may be positioned within or adjacent the pollution detection plane.

The measurement of crosswind integrated concentration by means of crosswind traverses of pollution sensing or collecting instrumentation is accomplished by any one of the following methods. These methods are illustrative and not exhaustive, and exemplify the various means whereby the method and technique of this invention can be realized in practice.

Figure 5:
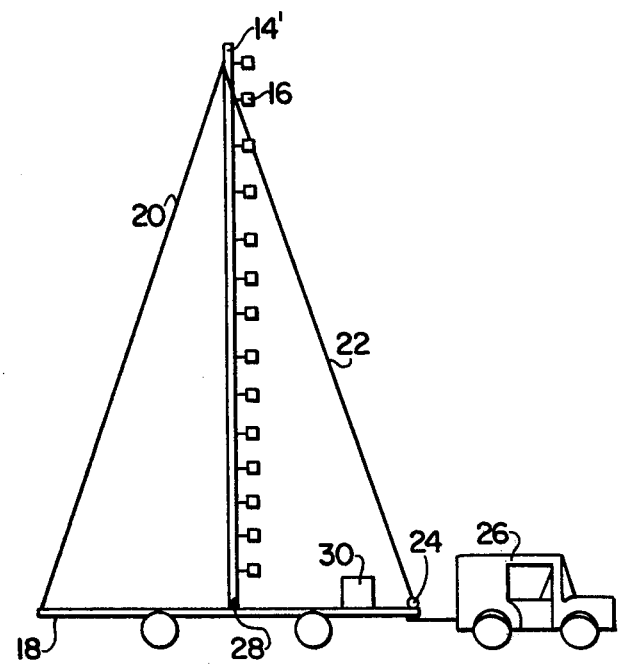
FIG. 5 is a side elevation, showing a towed, rigid mast carrying pollution sensing devices.

(a) As illustrated in FIG. 5 mechanical support of sampling instrumentation 16 is accomplished by use of an instrument mast 14', vertically mounted on trailer 18, by means of guys 20, 22. Trailer 18 may be pulled by a self-propelled vehicle 26. A conventional cable disconnect 24 may be employed for securing mast 14' as at pivot 28 for employing and servicing collectors 16'. The rig is moved with uniform velocity on a direction perpendicular to the mean wind. A vacuum pump and motor 30 may be mounted upon the vehicle or trailer for aspirating sample collectors. In case the available roads, trails or paths do not cross the wind exactly perpendicularly, the perpendicular component of the wind speed at each height is employed as the value of $u(z)$ in equation (13).

Figure 6:
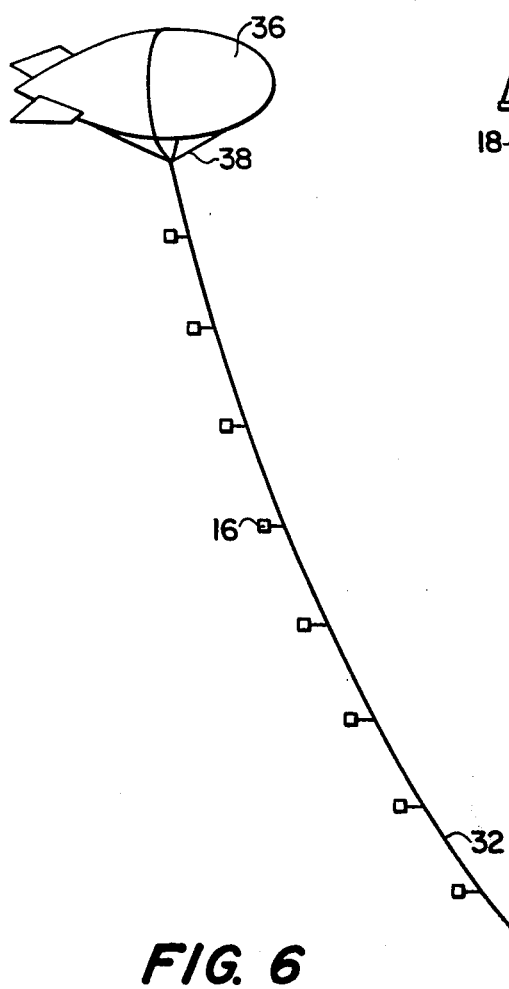
FIG. 6 is a side elevation, showing a balloon lifted cable, carrying pollution sensing devices.

(b) In FIG. 6 an alternative to rigid mast support is illustrated where greater heights are required than are feasible with a moving mast because of the vertical extent of the fugitive source, a vehicle-towed lighter-than-air balloon 36 with pulling harness 38 is used. In this case the sampling equipment is attached to balloon cable 32 at the appropriate heights regulated by winch 34, and the vacuum line required for sample collection is parallel to and attached to the balloon tether cable. Where individual motor and vacuum pump assemblies 30 are feasible in relation to balloon lift characteristics, an electric power line is carried alongside the tether cable.

Figure 7:
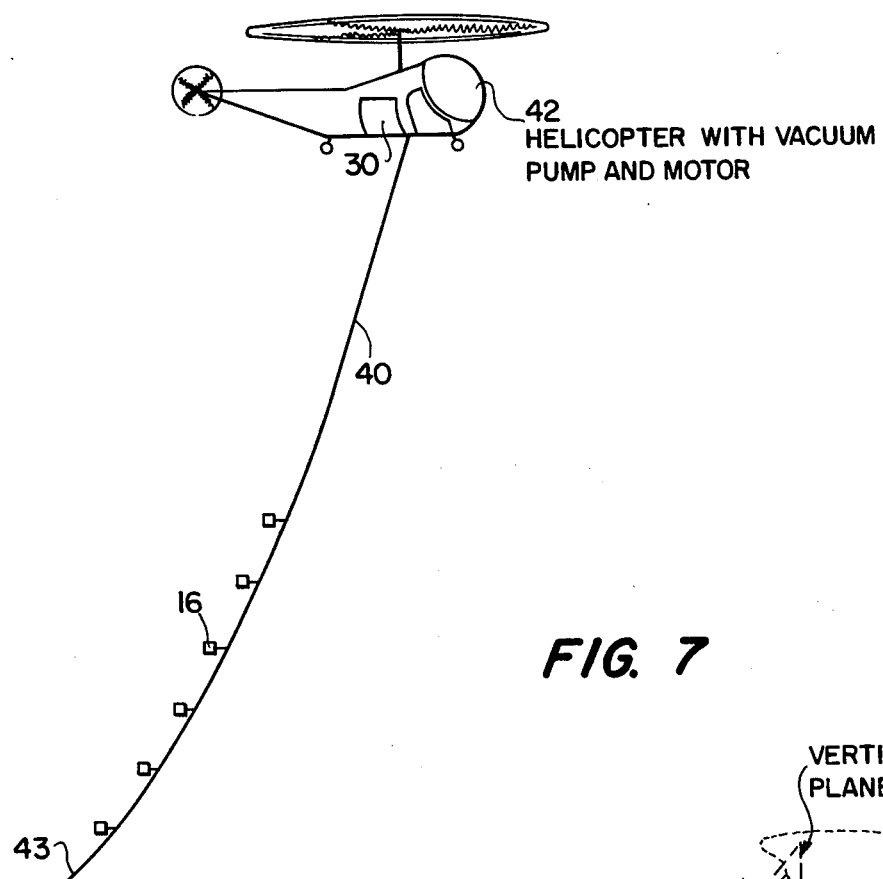
FIG. 7 is a side elevation, showing a helicopter lifted free ended cable, carrying pollution sensing devices.

(c) In FIG. 7 a further alternative employs a helicopter 42 from which a free end 43 of cable 40 is suspended, carrying the sampling instrumentation and associated vacuum pump or electrical line. An aerodynamic fish may be attached in order to stabilize the cable end. The helicopter is operated at an altitude sufficiently high above the sampled cloud that rotor downwash does not disturb the concentration distribution. Also, of course, that portion of cable 40 adjacent the helicopter is without sensors, such that downwash of the rotor will not affect sampling.

Figure 8:
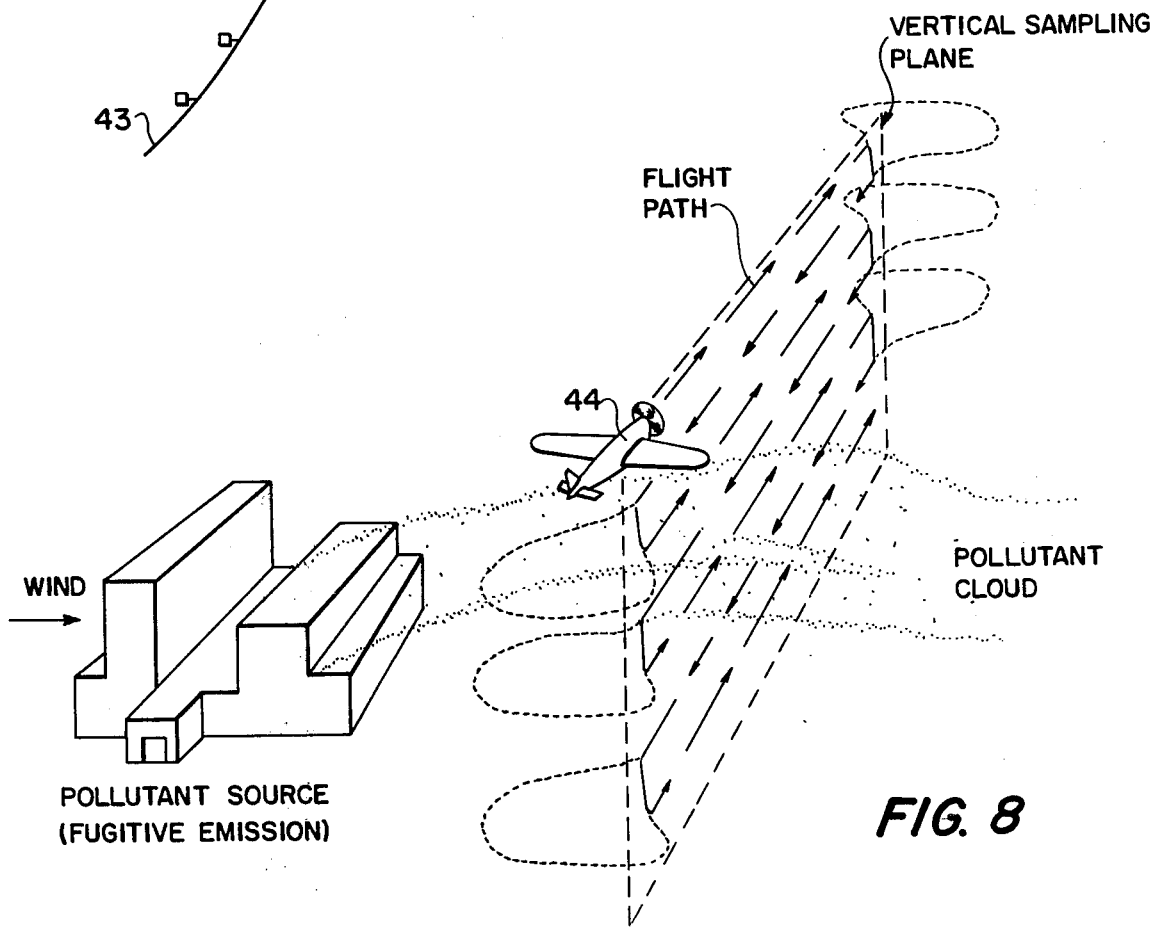
FIG. 8 is a schematic, showing fixed wing aircraft sensing in multiple passes through a pollution detection plane.

(d) In FIG. 8 a fixed wing aircraft 44 is illustrated, carrying a single sensor or sample collector, making successive passes at several heights. This approach is most useful when the scale of the pollutant cloud is large and the emission rate and wind conditions fairly constant, since the passes cannot be made concurrently.

Figure 9:
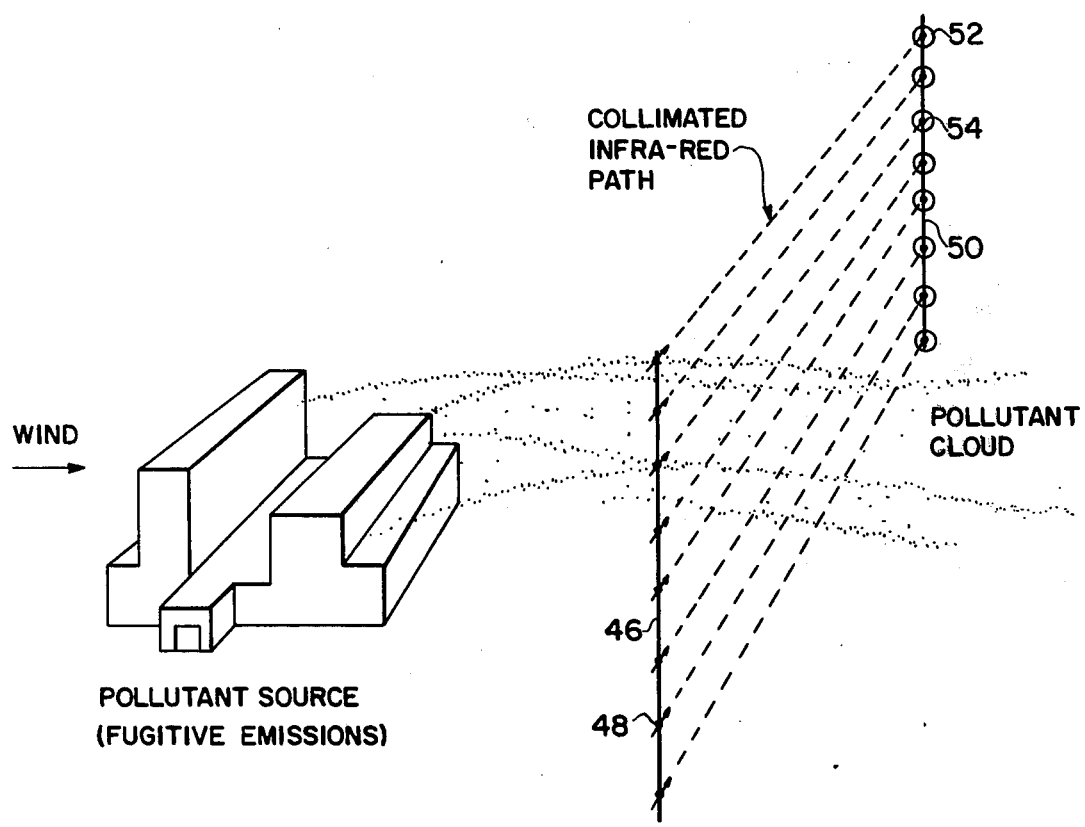
FIG. 9 is a schematic, showing a long path infra-red absorption method of measuring cross-wind integrated pollution concentration.

(e) In FIG. 9 crosswind integrated concentration is measured directly, and without the requirement for crosswind traverse with direct sensing of concentration or the collection of samples, by means of long path infra-red absorption methods. In this procedure two instrument masts 46, 50 are employed at the extremities of a crosswind line, with mast 46 carrying a series of vertically spaced infra-red radiation transmitters 48, filtered so as to transmit alternately in a frequency range which is selectively absorbed by the pollutant of interest but not by other ambient atmospheric constituents or other probable pollutants and in a frequency range which is not absorbed by the pollutant. The other mast 50, collimated with respect to mast 48, carries a matching series of infra-red receptors 54, positioned within parabolic concentrators 52. The attenuation of infra-red radiation represented by the differential energy in the two frequency ranges received by receptors 54 is related to the amount of pollutant in the transmission path, and therefore directly relatable to the crosswind integrated concentration. Continuous records of infra-red intensity received in the absorbing and non-absorbing frequencies permits evaluation of the history of time variation of source emission intensity. This feature of fugitive emissions is not attainable by any other method now known.

In all of the cases described above, a wind recording system is employed in the vicinity of the sampling line to obtain a vertical profile of wind speed and direction over the range of height being sampled, and during the time interval of sampling.

Repeated crosswind passes with the various vertical arrays of sampling instruments will provide estimates of the mean emission rate, and its variation. Repeated passes can also enable the collection of statistically significant amounts of pollutants when concentrations must be sampled which are low in relation to instrument sensitivity.

Comparable crosswind traverses made upwind of the source area being evaluated will serve to evaluate the contribution of incoming pollution to the apparent fugitive emission rate. This evaluation permits elimination of extraneous or exotic effects and, while conceptually similar in objective to the upwind-downwind method aforedescribed, is entirely different in application.

I claim:

1. Method of quantifying fugitive emission rates from pollution sources comprising:
   A. Gauging wind velocity and direction at an index point downwind of a pollution source;
   B. Outlining at said index point a pollution detection plane, said plane being oriented transversely with respect to the wind;
   C. Sensing pollutant concentration at a series of height intervals within the vertical and lateral confines of said pollution detection plane, so as to obtain integrated products of crosswind concentration and wind speed; and
   D. Displaying said products as a vertical profile of total mass flux of pollutant through said detection plane.

2. Method for quantifying fugitive emission rates into the atmosphere from pollution sources as in claim 1, wherein said outlining of said pollution detection plane is such that the vertical and lateral dimensions of said plane encompass a substantial portion of pollutant flux emanating from said pollution source.

3. Method for quantifying fugitive emission rates into the atmosphere from pollution sources as in claim 2, wherein said outlining is such that the vertical and lateral dimensions of said pollution detection plane coincide with said vertical profile of pollutant flux.

4. Method for quantifying fugitive emission rates into the atmosphere from pollution sources as in claim 2, wherein said index point is sufficiently close to said pollution source such that said vertical profile of pollutant flux in said pollution detection plane is similar to the vertical profile of pollutant flux at said pollution source.

5. Method of quantifying fugitive emission rates into the atmosphere from pollution sources as in claim 1, wherein said gauging of wind is at vertically spaced points adjacent said pollution detection plane and is aligned with the axis thereof.

6. Method of quantifying fugitive emission rates into the atmosphere from pollution sources as in claim 5, wherein said sensing of pollutant concentration at a series of height intervals is accomplished simultaneously at spaced vertical points within said pollution detection plane.

7. Method of quantifying fugitive emission rates into the atmosphere from pollution sources as in claim 6, wherein said sensing within the lateral and vertical confines of said plane is accomplished sequentially cross wind within said pollution detection plane.

8. Method of quantifying fugitive emission rates into the atmosphere from pollution sources as in claim 7, wherein said sensing is by lifting while moving sensing devices within the lateral and vertical confines of said pollution detection plane.

9. Method of quantifying fugitive emission rates into the atmosphere from pollution sources as in claim 6, including infra-red sensing of said fugitive emissions.

10. Method of quantifying fugitive emission rates into the atmosphere from pollution sources as in claim 9, wherein said infra-red sensing is correlated with elapsed time, as a measure of variation in fugitive emission intensity.

11. Method of quantifying fugitive emission rates into the atmosphere from pollution sources as in claim 10, wherein said infra-red sensing is correlated with both elapsed time and wind speed, as a measure of fugitive emission intensity.

12. Method of quantifying fugitive emission rates into the atmosphere from pollution sources as in claim 5, including comparing downwind quantifying with similar upwind quantifying so as to relate incoming pollution with apparent fugitive emission rates.

13. Method of quantifying fugitive emission rates into the atmosphere from pollution sources as in claim 5, wherein said sensing of pollutant concentration is accomplished sequentially at spaced vertical points within said pollution detection plane.

14. Method of quantifying fugitive emission rates into the atmosphere from pollution sources as in claim 5, wherein said sensing at vertically spaced points within said pollution detection plane is by traversing said plane from side to side.

15. Method of quantifying fugitive emission rates into the atmosphere from pollution sources as in claim 14, wherein said traversing is at a speed such that the concentration of pollutant is approximately constant.

16. Method of quantifying fugitive emission rates into the atmosphere from pollution sources as in claim 14, including reorienting said pollution detection plane, according to changes in wind direction.

* * * * *